(12) United States Patent
Nelson et al.

(10) Patent No.: US 7,033,762 B2
(45) Date of Patent: *Apr. 25, 2006

(54) SINGLE NUCLEOTIDE AMPLIFICATION AND DETECTION BY POLYMERASE

(75) Inventors: John Nelson, Neshanic Station, NJ (US); Carl Fuller, Berkeley Heights, NJ (US); Anup Sood, Flemington, NJ (US); Shiv Kumar, Belle Mead, NJ (US)

(73) Assignee: Amersham Biosciences Corp, Piscataway, NJ (US)

( * ) Notice: Subject to any disclaimer, the term of this patent is extended or adjusted under 35 U.S.C. 154(b) by 540 days.

This patent is subject to a terminal disclaimer.

(21) Appl. No.: 10/113,025

(22) Filed: Apr. 1, 2002

(65) Prior Publication Data

US 2003/0096253 A1    May 22, 2003

Related U.S. Application Data

(60) Provisional application No. 60/315,798, filed on Aug. 29, 2001.

(51) Int. Cl.
*C12Q 1/68* (2006.01)

(52) U.S. Cl. .......................................... 435/6
(58) Field of Classification Search .................. 435/6, 435/7, 91.2; 436/501
See application file for complete search history.

(56) References Cited

U.S. PATENT DOCUMENTS

| | | | |
|---|---|---|---|
| 5,849,487 A | 12/1998 | Hase et al. | |
| 6,187,286 B1 | 2/2001 | Elmaleh et al. | |
| 2003/0064366 A1* | 4/2003 | Hardin et al. .................. | 435/6 |

FOREIGN PATENT DOCUMENTS

| | | |
|---|---|---|
| WO | WO 96/22297 | 7/1996 |
| WO | WO 99/16832 | 4/1999 |
| WO | WO 02/40126 | 5/2002 |
| WO | WO 03/020734 | 3/2003 |
| WO | WO 03/020891 | 3/2003 |

OTHER PUBLICATIONS

Newton, C. R., et al. "The Production of PCR Products with 5' Single-Stranded Tails Using Primers that Incorporate Novel Phosphoramidite Intermediates" Nucleic Acid Research, Oxford University Press, Surrey, GB, vol. 21, No. 5, 1993, pp. 1155-1162.

Dyatkina, N., et al. "Modified Triphosphates of carbocyclic nucleoside analogues: synthesis, stability towards alkaline phosphatase and substrate properties for some DNA polymerases" Bioorganic and Medicinal Chemistry Letters, Oxford, GB, vol. 6, No. 22, Nov. 19, 1996, pp. 2639-2642.

Su, S-H., et al. "Novel non-nucleosidic phosphoramidites for oligonucleotide modification and labeling" Bioorganic and Medicinal Chemistry Letters, Oxford, GB, vol. 7, No. 13, Jul. 8, 1997, pp. 1639-1644.

Arzumanov Andrey, A., et al. "Gamma-Phosphate-substituted 2'-deoxynucleoside 5'triphosphates as substrates for DNA polymerases" Journal of Biological Chemistry, vol. 271, No. 40, 1996, pp. 24389-24394.

* cited by examiner

*Primary Examiner*—Jeffrey Fredman
*Assistant Examiner*—Heather G. Calamita
(74) *Attorney, Agent, or Firm*—Royal N. Ronning, Jr.; Yonggang Ji

(57) ABSTRACT

A method of characterizing a nucleic acid sample is provided that includes the steps of: (a) conducting a DNA polymerase reaction that includes the reaction of a template, a non-hydrolyzable primer, at least one terminal phosphate-labeled nucleotide, DNA polymerase, and an enzyme having 3'→5' exonuclease activity which reaction results in the production of labeled polyphosphate; (b) permitting the labeled polyphosphate to react with a phosphatase to produce a detectable species characteristic of the sample; (c) detecting the detectable species; and (d) characterizing the nucleic acid sample based on the detection.

46 Claims, 3 Drawing Sheets

```
                        SEQUENCE LISTING

<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Primer for DNA Amplification

<400> SEQUENCE: 1
gttttcccag tcacgacgtt gta                                              23

<210> SEQ ID NO 2
<211> LENGTH: 30
<212> TYPE: DNA
<213> ORGANISM: Artificial Sequence
<220> FEATURE:
<223> OTHER INFORMATION: DNA Template
<221> NAME/KEY: misc_difference
<222> LOCATION: (30)..(30)
<223> OTHER INFORMATION: Dideoxynucleotide in 3'-most position

<400> SEQUENCE: 2
gtcgttatac aacgtcgtga ctgggaaaac                                       30

<210> SEQ ID NO 3
<211> LENGTH: 30
<212> TYPE: DNA
<213> ORGANISM: Artificial Sequence
<220> FEATURE:
<223> OTHER INFORMATION: DNA Template
<221> NAME/KEY: misc_difference
<222> LOCATION: (30)..(30)
<223> OTHER INFORMATION: Dideoxynucleotide in 3'-most position

<400> SEQUENCE: 3
gtcgttctac aacgtcgtga ctgggaaaac                                       30
```

SINGLE NUCLEOTIDE AMPLIFICATION AND DETECTION BY POLYMERASE

RELATED APPLICATIONS

This application claims priority benefit under Title 35 §119(e) of U.S. Provisional Application No. 60/315,798, filed Aug. 29, 2001.

FIELD OF THE INVENTION

The present invention relates generally to methods of detecting and characterizing a polynucleotide in a sample, based on the use of a non-hydrolyzable primer and terminal-phosphate-labeled nucleotides as substrates for DNA polymerase. The invention further relates to a method of detecting a mutation of a specific nucleotide base in a target polynucleotide. The labels employed are enzyme-activatable and include chemiluminescent, fluorescent, electrochemical and chromophoric moieties as well as mass-tags.

BACKGROUND OF THE INVENTION

Methods are known for detecting specific nucleic acids or analytes in a sample with high specificity and sensitivity. A method of analysis which is based on the complimentarily between nucleotide sequences allows for the direct analysis of genetic characters. This provides a very useful means for identifying genetic disorders or a carcinomatous change of normal cells.

However, detection and characterization of a trace amount of a target nucleotide in a sample is difficult. Therefore, methods for direct detection of the gene generally require first amplifying a nucleic acid sequence based on the presence of a specific target sequence or analyte. Following amplification, the amplified sequences are detected and quantified. Conventional detection systems for nucleic acids include detection of fluorescent labels, fluorescent enzyme-linked detection systems, antibody-mediated label detection, and detection of radioactive labels.

As a method of amplifying a nucleic acid sequence, the PCR (polymerase chain reaction) process is known. Presently, the PCR is the most conventional means for in vitro amplification of nucleic acid. However, the PCR has certain disadvantages, including the requirement for strict temperature control, inadequate quantification due to logarithmic amplification, and the danger of erroneous results brought about by simultaneous amplification of trace amounts of contaminated DNA.

In addition to amplification methods which involve detection and quantification of the sequences, there are signal amplification methods which detect amplified decomposition products, i.e., a product or by-product of a reaction is amplified as the signal from a target nucleic acid.

For example, a cycling assay has been developed which utilizes λ-exonuclease to specifically cleave double stranded DNA (C. G. Copley et al., Bio Techniques, Vol. 13, No. 6, pp 882–892, 1992). This method involves hybridizing an oligonucleotide probe with a nucleic acid sequence complimentary thereto, allowing λ-exonuclease to act on the formed double-stranded DNA to decompose the hybridized probe. The probe is replaced by another probe, which is then decomposed. In this way, a cycling reaction repeats. In this method, the presence of a target DNA sequence is estimated by the detection of the decomposed probe. A disadvantage of this method is that the λ-exonuclease requires a probe which is phosphorylated at its 5'-terminal as the substrate. Following chemical synthesis of the probe by known methods, the 5'-terminal needs to be phosphorylated, and it is often difficult to confirm that all 5'-terminals are phosphorylated completely. An additional problem of this method is the low turnover number of cycling reactions, i.e., the number of times hybridization between the primer and target nucleotide occurs. The turnover number is low since the hybridization step must repeatedly occur.

An additional cycling assay by an exonuclease has been disclosed in EP 500224/A1. In this method, the synthesis of a DNA strand complimentary to a target DNA proceeds from a primer simultaneously with the decomposition of the same primer from the other side by a 5'→3' exonuclease such that another primer hybridizes with the target sequence in place of the decomposed primer hybridized before. Therefore, in a single cycle reaction both the synthesis of a complimentary strand by DNA polymerase as well as the degradation of the synthesized strand repeatedly occurs. A disadvantage of this method is the low turnover number, with the hybridization step being rate limiting in that it must repeatedly occur.

A further cycling assay for detection of a polynucleotide containing a specific sequence is disclosed in U.S. Pat. No. 5,849,487. This method relies on signal amplification and detection of decomposition products. This method includes using a combination of nucleic acid polymerase, 3'→5' exonuclease, a nuclease-resistant primer, a target nucleic acid, which may be DNA at limiting concentration, and at least one deoxynucleoside triphosphate (dNTP) to detect the target nucleic acid sequence. The method further includes synthesizing a complimentary strand being a nucleotide species located adjacent to the 3'-terminal of the nuclease-resistant primer, followed by decomposition of the nucleotide species joined to the end of the primer and detection of the resulting pyrophosphoric acid or deoxynucleoside monophosphate, the synthesis and decomposition of the nucleotide species being repeated one or more times. A disadvantage of this method as well as other detection methods presently widely in use is the need to separate labeled starting material from a final labeled product or by-product. Such separations generally require gel electrophoresis or immobilization of a target nucleic acid sequence onto a membrane for detection. For example, in U.S. Pat. No. 5,849,487, the deoxynucleoside monophosphate formed by a nuclease reaction is separated by chromatography and optically measured. Alternatively, the pyrophosphoric acid which is formed upon incorporation of a complimentary base by DNA polymerase may be allowed to react with adenosine-5'-phosphosulfate and adenosine triphosphate sulfurase to form adenosine triphosphate, which is then detected using a luciferin-luciferase reaction; this presents the disadvantage of requiring additional reagents and incubation steps.

Moreover, U.S. Pat. No. 5,849,487 uses only the presence or absence of a nucleotide species remaining after nuclease digestion to detect a mutation of a specific nucleotide base in the target. That is to say, the nucleotide will join onto the 3' end of the primer only if a specific base is, or is not, the mutation to be detected. The patent fails to disclose a method to identify the actual mutation present by first analysis.

It has been known that DNA and RNA polymerases are able to recognize and utilize nucleosides with a modification at or in place of the gamma position of the triphosphate moiety. It is further known that the ability of various polymerases to recognize and utilize gamma-modified nucleoside triphosphates appears to vary depending on the moiety attached to the gamma phosphate.

A colorimetric assay for monitoring RNA synthesis from RNA polymerases in the presence of a gamma-phosphate modified nucleotide has been reported (Ref. Vassiliou W, Epp J B, Wang B B, Del Vecchio A M, Widlanski T, Kao C C. Exploiting polymerase promiscuity: A simple colorimetric RNA polymerase assay. Virology. Sep. 1, 2000; 274(2): 429–37). In this report, RNA polymerase reactions were performed in the presence of a gamma-modified, alkaline phosphatase resistant nucleoside triphosphate which was modified at its gamma phosphate with a dinitrophenyl group. When RNA polymerase reactions were performed in the presence of this gamma-modified NTP as the sole nucleoside triphosphate and a homopolymeric template, it was found that RNA polymerase could recognize and utilize the modified NTP. Moreover, when the polymerase reactions were performed in the presence of an alkaline phosphatase, which digested the p-nitrophenyl pyrophosphate aldo-product of a phosphoryl transfer to the chromogenic p-nitrophenylate, an increase in absorbance was reported. A disadvantage of this detection method is that the real-time colorimetric assay, performed in the presence of an alkaline phosphatase, only works with a homopolymeric template.

It would, therefore, be of benefit to provide methods of detecting and characterizing a nucleic acid, which methods would include utilization of terminal-phosphate-labeled nucleotides as substrates for DNA polymerase in a cycling assay by an exonuclease. It would further be of benefit if such methods would employ enzyme-activatable labels at the terminal phosphate of the nucleotide for production of an amplified detectable species from a target nucleic acid which would eliminate the need to separate labeled starting materials from labeled products or by-products. Moreover, it would be highly desirable if such methods for detecting and characterizing nucleic acids would allow for real-time monitoring of a heteropolymeric target nucleic acid using routine lab instrumentation.

SUMMARY OF THE INVENTION

An aspect of the present invention is to provide a method of detecting a polynucleotide in which a 3'→5' DNA exonuclease acting on DNA, is used together with DNA polymerase and a phosphatase so that a signal from the target nucleotide can be amplified and detected without the need for further operations such as separation of labeled reaction products from labeled starting materials.

The present invention provides methods for detecting a nucleic acid sample. One method includes the steps of: (a) conducting a DNA polymerase reaction, the reaction including the reaction of a template, a non-hydrolyzable primer, at least one terminal phosphate-labeled nucleotide, DNA polymerase and an enzyme having 3'→5' exonuclease activity, wherein the enzyme may be selected from DNA polymerases, exonucleases, and combinations thereof, which reaction results in the production of labeled polyphosphate; (b) permitting the labeled polyphosphate to react with a phosphatase to produce a detectable species; and (c) detecting the detectable species.

Further provided is a method of detecting a nucleic acid sample including the steps of: (a) conducting a DNA polymerase reaction, the reaction comprising the reaction of a template, a non-hydrolyzable primer, at least one terminal phosphate-labeled nucleotide having 4 or more phosphate groups in the polyphosphate chain, DNA polymerase and an enzyme having 3'→5' exonuclease activity, wherein the enzyme may be selected from DNA polymerases, exonucleases and combinations thereof, which reaction results in the production of labeled polyphosphate; and (b) detecting the labeled polyphosphate.

Another aspect of the invention relates to a method of detecting a nucleic acid sample comprising the steps of: (a) conducting a DNA polymerase reaction, the reaction comprising the reaction of a template, a non-hydrolyzable primer, at least one terminal phosphate-labeled nucleotide having 4 or more phosphate groups in the polyphosphate chain, DNA polymerase and an enzyme having 3'→5' exonuclease activity, wherein the enzyme may be selected from DNA polymerases, exonucleases and combinations thereof, which reaction results in the production of labeled polyphosphate; (b) permitting the labeled polyphosphate to react with a phosphatase to produce a detectable species; and (c) detecting the detectable species.

The invention further provides methods of characterizing a nucleic acid sample. For example, the invention provides a method including the steps of: (a) conducting a DNA polymerase reaction, the reaction including the reaction of a template, a non-hydrolyzable primer, at least one terminal phosphate-labeled nucleotide, DNA polymerase and an enzyme having 3'→5' exonuclease activity, wherein the enzyme may be a DNA polymerase, exonuclease or a combination thereof, which reaction results in the production of labeled polyphosphate; (b) permitting the labeled polyphosphate to react with a phosphatase to produce a detectable species; (c) detecting the detectable species; and (d) characterizing the nucleic acid based on the detection.

Further encompassed by the invention is a method of characterizing a nucleic acid sample including the steps of: (a) conducting a DNA polymerase reaction, the reaction comprising the reaction of a template, a non-hydrolyzable primer, at least one terminal phosphate-labeled nucleotide having 4 or more phosphate groups in the polyphosphate chain, DNA polymerase and an enzyme having 3'→5' exonuclease activity, wherein the enzyme may be selected from DNA polymerases, exonucleases and combinations thereof, which reaction results in the production of labeled polyphosphate; (b) detecting said labeled polyphosphate; and (c) characterizing the nucleic acid sample based on the detection.

Also provided is a method of characterizing a nucleic acid sample including the steps of: (a) conducting a DNA polymerase reaction, the reaction comprising the reaction of a template, a non-hydrolyzable primer, at least one terminal phosphate-labeled nucleotide having 4 or more phosphate groups in the polyphosphate chain, DNA polymerase and an enzyme having 3'→5' exonuclease activity, wherein the enzyme may be selected from DNA polymerases, exonucleases and combinations thereof, which reaction results in the production of labeled polyphosphate; (b) permitting the labeled polyphosphate to react with an alkaline phosphatase to produce a detectable species having a signal profile characteristic of the sample; (c) detecting the detectable species; and (d) characterizing the nucleic acid sample based on the signal profile.

Moreover, the present invention provides methods of detecting a mutation of a specific nucleotide base in a target nucleic chain. One inventive method includes the steps of: (a) conducting a DNA polymerase reaction, the reaction including the reaction of a template, a non-hydrolyzable primer, at least one terminal phosphate-labeled nucleotide, DNA polymerase and an enzyme having 3'→5' exonuclease activity, wherein the enzyme may be selected from DNA polymerases, exonucleases and combinations thereof, which reaction results in the production of labeled polyphosphate;

(b) permitting the labeled polyphosphate to react with a phosphatase to produce a detectable species having a unique signal profile; (c) detecting the detectable species; and (d) characterizing the mutation in the nucleic acid sequence based on the presence or absence of the detectable species and the unique signal profile thereof.

Additionally provided is a method of detecting a mutation of a specific nucleotide base in a target nucleic acid sequence which includes the following steps: (a) conducting a DNA polymerase reaction, the reaction comprising the reaction of a template, a non-hydrolyzable primer, at least one terminal phosphate-labeled nucleotide having 4 or more phosphate groups in the polyphosphate chain, DNA polymerase and an enzyme having 3'→5' exonuclease activity, wherein the enzyme may be selected from DNA polymerases, exonucleases and combinations thereof, which reaction results in the production of labeled polyphosphate if the terminal phosphate-labeled nucleotide is complimentary to the specific base; (b) detecting the labeled polyphosphate; and (c) characterizing the mutation in the nucleic acid sequence based on the presence or absence of the labeled polyphosphate.

Further encompassed by the invention is a method of detecting a mutation of a specific nucleotide base in a target nucleic acid sequence including the steps of: (a) conducting a DNA polymerase reaction, the reaction comprising the reaction of a template, a non-hydrolyzable primer, at least one terminal phosphate-labeled nucleotide having 4 or more phosphate groups in the polyphosphate chain, DNA polymerase and an enzyme having 3'→5' exonuclease activity, wherein the enzyme may be selected from the group consisting of DNA polymerases, exonucleases and combinations thereof, which reaction results in the production of labeled polyphosphate if the terminal phosphate-labeled nucleotide is complimentary to the specific base; (b) permitting the labeled polyphosphate to react with an alkaline phosphatase to produce a detectable species having a unique signal profile; (c) detecting the detectable species; and (d) characterizing the mutation in the nucleic acid sequence based on the presence or absence of the detectable species and on the unique signal profile thereof.

Kits for detecting a polynucleotide are further provided by the invention, one kit including: (a) at least one terminal-phosphate-labeled nucleotide; (b) a DNA polymerase; (c) a phosphatase; and (d) a nuclease with enzymatic activity sufficient to decompose DNA in the 3'→5' direction.

A further kit for detection of a polynucleotide is provided which includes: (a) at least one terminal-phosphate-labeled nucleotide; (b) a phosphatase; and (c) a DNA polymerase with enzymatic activity sufficient to decompose DNA in the 3'→5' direction.

A further aspect of the present invention is to provide a kit for the detection of a mutation of a specific nucleotide base in a target nucleic acid chain, one kit including: (a) at least one terminal-phosphate-labeled nucleotide; (b) a DNA polymerase; (c) a phosphatase; and (d) a nuclease with enzymatic activity sufficient to decompose DNA in the 3'→5' direction.

Lastly, a kit is provided herein for the detection of a mutation of a specific nucleotide base in a target nucleic acid chain which includes: (a) at least one terminal-phosphate-labeled nucleotide; (b) a phosphatase; and (c) a DNA polymerase with enzymatic activity sufficient to decompose DNA in a 3'→5' direction.

DESCRIPTION OF THE INVENTION

Figure 1:
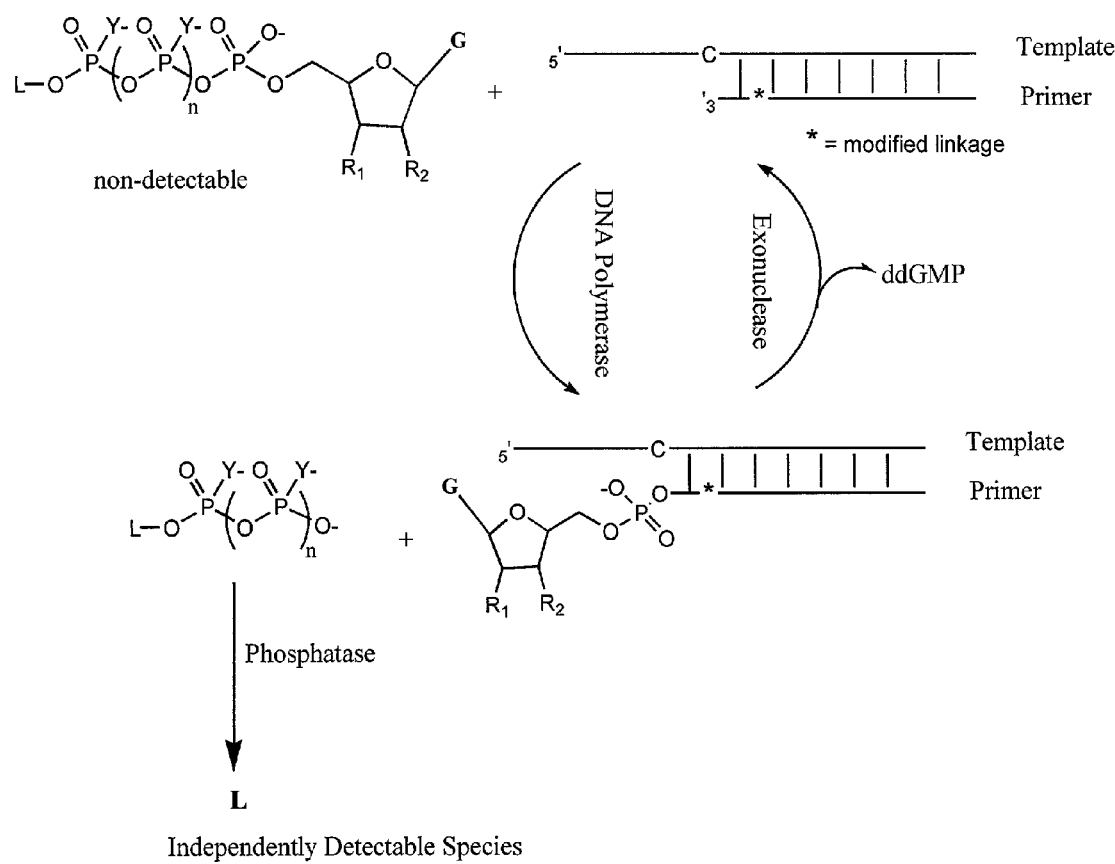
FIG. 1 shows an embodiment of a method of the present invention where a terminal-phosphate-labeled nucleotide complimentary in sequence to a target polynucleotide is joined to the 3' end of a nuclease-resistant primer, followed by decomposition thereof to effect a cycling assay in which the labeled polyphosphate by-product of nucleotide incorporation reacts with an alkaline phosphatase to produce a detectable species.

The term "nucleoside" as defined herein is a compound including a purine deazapurine, or pyrimidine base linked to a sugar or a sugar substitute, such as a carbocyclic or acyclic linker at the 1' position or equivalent position and includes 2'-deoxy and 2'-hydroxyl, 2', 3'-dideoxy forms, as well as other substitutions.

The term "nucleotide" as used herein refers to a phosphate ester of a nucleoside, wherein the esterification site typically corresponds to the hydroxyl group attached to the C-5 position of the pentose sugar.

The term "oligonucleotide" includes linear oligomers of nucleotides or derivatives thereof, including deoxyribonucleosides, ribonucleosides, and the like. Throughout the specification, whenever an oligonucleotide is represented by a sequence of letters, the nucleotides are in the 5'→3' order from left to right where A denotes deoxyadenosine, C denotes deoxycytidine, G denotes deoxyguanosine, and T denotes thymidine, unless noted otherwise.

The term "primer" refers to a linear oligonucleotide that anneals in a specific way to a unique nucleic acid sequence and allows for amplification of that unique sequence.

The phrase "target nucleic acid sequence" and the like refers to a nucleic acid whose sequence identity, or ordering or location of nucleosides is determined by one or more of the methods of the present invention.

The present invention relates to methods of detecting and characterizing the polynucleotide in a sample wherein a convenient assay is used for monitoring the addition of a terminal-phosphate-labeled nucleotide which is complimentary to a specific base in the target polynucleotide, onto the 3'-terminal of a non-hydrolyzable primer followed by nuclease decomposition thereof. DNA polymerases synthesize oligonucleotides via transfer of a nucleoside monophosphate from a deoxynucleoside triphosphate (dNTP) to the 3' hydroxyl of a growing oligonucleotide chain.

The force which drives this reaction is the cleavage of an anhydride bond and the con-commitant formation of an inorganic pyrophosphate. The present invention utilizes the finding that structural modification of the terminal-phosphate of the nucleotide does not abolish its ability to function in the polymerase reaction. The oligonucleotide synthesis reaction involves direct changes only at the α- and β-phosphoryl groups of the nucleotide, allowing nucleotides with modifications at the terminal phosphate position to be valuable as substrates for nucleic acid polymerase reactions.

The methods provided by this invention utilize a nucleoside polyphosphate analogue, such as a deoxynucleoside polyphosphate or dideoxynucleoside polyphosphate analogue with an electrochemical label, mass tag, or a chromogenic, chemiluminescent, or fluorescent dye label attached to the terminal-phosphate. When a nucleic acid polymerase uses this analogue as a substrate, an enzyme-activatable label is present on the inorganic polyphosphate by-product of phosphoryl transfer. Cleavage of the polyphosphate product of phosphoryl transfer by a phosphatase, results in a detectable change in the label attached thereon. For example, if 3-cyanoumbelliferone dye is attached via its hydroxyl group to the terminal phosphate position of a nucleotide, the dye is not fluorescent when excited at 408 nm and it is not a substrate for alkaline phosphatase. Once this nucleotide is incorporated into DNA, the released dye inorganic polyphosphate (which also is not fluorescent when excited at 408 nm) is a substrate for alkaline phosphatase. Once de-phosphorylated, the dye becomes fluorescent when excited at 408 nm and hence detectable. The specific analysis of the polyphosphate product can be carried out in the same reaction solution as, the polymerase and exonuclease reactions, with no need to separate reaction products from starting materials. This allows for the detection and, optionally, quantitation of nucleic acids formed during polymerase reactions using routine instrumentation such as fluorimeters or spectrophotometers.

It is noted that while RNA and DNA polymerases are able to recognize nucleotides with modified terminal phosphoryl groups, the inventors have determined that this starting material is not a substrate for phosphatases. The scheme below shows relevant molecules in the method of this invention; namely the terminal-phosphate-labeled nucleotide, the labeled polyphosphate by-product and the enzyme-activated label.

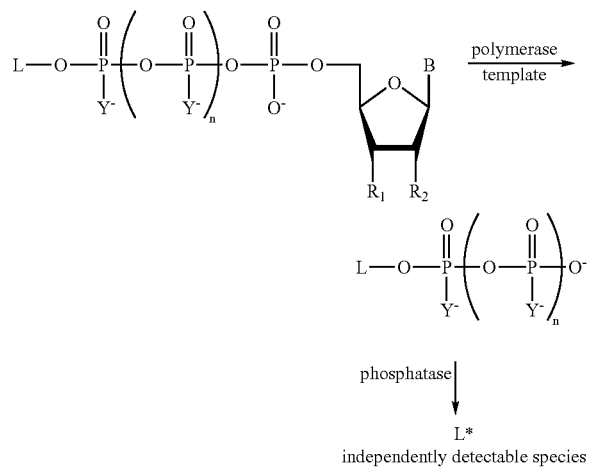

In the scheme above, n is 1 or greater, $R_1$ and $R_2$ are independently H, SH, SR, F, Br, Cl, I, $N_3$, $NH_2$, NHR, OR or OH; B is a natural or modified nucleoside base; X is O, S, or NH; Y is O, S, or $BH_3$ and L is a phosphatase activatable label which may be a chromogenic, fluorogenic, or chemiluminescent molecule, mass tag or electrochemically detectable moiety. A mass tag is a small molecular weight moiety suitable for mass spectrometry that is readily distinguishable from other reaction products due to difference in mass. An electrochemical tag is an easily oxidizable or reducible species. It has been discovered that when n is 2 or greater, the nucleotides are significantly better substrates for polymerases than when n is 1. Therefore, in preferred embodiments of the present invention, n is 2, 3 or 4. In further desired embodiments of the present invention, X and Y are O; and $R_1$ and $R_2$ are independently H or OH; B is a nucleotide base and L is a label which may be a chromogenic, fluorogenic or a chemiluminescent molecule.

In one embodiment of the method of detecting a nucleic acid sequence provided herein, the steps include conducting a DNA polymerase reaction, the reaction including the reaction of a template, a non-hydrolyzable primer, at least one terminal phosphate-labeled nucleotide, DNA polymerase and an enzyme having 3'→5' exonuclease activity, wherein the enzyme may be selected from DNA polymerases, exonucleases and combinations thereof, which reaction results in the production of labeled polyphosphate provided the terminal phosphate-labeled nucleotide is complementary to the template; permitting the labeled polyphosphate to react with a phosphatase, such as alkaline phosphatase, to produce a detectable species; and detecting the detectable species.

In the methods of characterizing nucleic acid sample provided by this invention, the target nucleic acid may be characterized by determining the presence or absence of the detectable species. Moreover, the detectable species may have a characteristic staining profile or signal profile associated with it, the profile being characteristic of the sample. This allows for characterization of the nucleic acid target based on the unique profile of the detectable species.

One particular characterization of a target nucleic acid may include the detection of a mutation of a specific nucleotide base in a target nucleic acid sequence. A method of detecting a mutation provided herein includes the steps of: (a) conducting a DNA polymerase reaction, the reaction including the reaction of a template, a non-hydrolyzable primer, at least one terminal phosphate-labeled nucleotide, DNA polymerase, and an enzyme having 3'→5' exonuclease activity, wherein the enzyme may be selected from DNA polymerases, exonucleases and combinations thereof, which reaction results in the production of labeled polyphosphate; (b) permitting the labeled polyphosphate to react with a phosphatase to produce a detectable species having a unique signal profile; (c) detecting the detectable species; and (d) characterizing the mutation in the nucleic acid sequence based on the presence or absence of the detectable species and on the unique signal profile thereof.

FIG. 1 shows the general scheme employed for each of the methods described above. In this scheme, n is 1 or greater, $R_1$ and $R_2$ are independently H, OH, SH, SR, F, Cl, Br, I, $N_3$, $NH_2$ or OR; G is guanine, or representative of a natural or modified nucleoside base; C is cytosine or representative of the base complimentary to the added nucleotide; Y is O, S, or $BH_3$ and L is a chromogenic, fluorogenic, chemiluminescent, or electrochemical label or mass tag which preferably becomes independently detectable when the phosphate is removed. As shown in FIG. 1, a target polynucleotide is hybridized with a nuclease-resistant, non-hydrolyzable polynucleotide primer having a sequence complementary at least in part to the target polynucleotide. The DNA polymerase reaction is conducted in the presence of the formed hybrid and at least one terminal-phosphate-labeled nucleotide under conditions to cause a nucleoside monophosphate derived from the terminal-phosphate-labeled nucleotide to join to the 3'-terminal end of the nuclease-resistant primer if it is complementary to the target polynucleotide. This is accompanied by the concomitant formation of a labeled product which may not be independently detectable. The labeled polyphosphate concomitantly formed during incorporation of the nucleotide species is permitted to react with a phosphatase to produce an independently detectable species which serves as the signal from the target polynucleotide. Addition of a complimentary nucleotide species to the 3'-terminal of the primer is followed by decomposition thereof by the reaction of a 3'→5' exonuclease which may be associated with the DNA polymerase itself. The synthesis and decomposition of the complementary strand being essentially the nucleotide species, is repeated one or more times to effect a cycling assay.

In the methods described above, the polymerase reaction may be conducted in the presence of a phosphatase, such as alkaline phosphatase, which converts the labeled polyphosphate product to the detectable label. As such, convenient assays are established for detecting and characterizing a nucleic acid that allows for continuous, real-time monitoring of detectable species formation. This represents a homogeneous assay format in that it can be performed in a single tube.

It is noted that in embodiments including terminal phosphate-labeled nucleotides having four or more phosphates in the polyphosphate chain, it is within the contemplation of the present invention that the labeled polyphosphate by-product of phosphoryl transfer may be detected without the use of phosphatase treatment. For example, it is known that natural or modified nucleoside bases, particularly guanine, can cause quenching of fluorescent markers. Therefore, in a terminal phosphate labeled nucleotide, the label may be partially quenched by the base. Upon incorporation of the nucleoside monophosphate, the labeled polyphosphate by-product may be detected due to its enhanced fluorescence. Alternatively, it is possible to physically separate the labeled polyphosphate product by chromatographic separation methods before identification by fluorescence, color, chemiluminescence, or electrochemical detection. In addition, mass spectometry could be used to detect the products by mass difference.

The detectable species may be produced in amounts substantially proportional to the amount of target nucleic acid and, as such, is a signal for the amount of the target nucleic acid. The methods herein described may further include the step of quantifying the target nucleic acid based on the amount of detectable species produced during the reaction. The step of quantifying the target nucleic acid sequence is desired to be done by comparison of spectra produced by the detectable species with known target quantities.

In the present invention, once hybridized, the oligonucleotide primer can repeatedly function so as to permit the reaction to proceed quantitatively in an at least equal molar amount relative to the template nucleotide sequence. The amount of the oligonucleotide primer useful in the methods of the present invention should be that sufficient to attain a favorable hybridization. In general, a sensitive assay can be attained by the presence of a primer which is at least equal molar and desirably in a 5-fold excess relative to the intended range of detection.

The methods provided by the present invention may further include the step of including one or more additional detection agents in the DNA polymerase reaction. The additional detection agent may be capable of a response which is detectably different from the detectable species. For example, the additional detection agent may be an antibody.

The target nucleic acid of the present invention includes, but is not limited to, chromosomal DNA, RNA, mRNA, virus- or mRNA-derived cDNA, or a natural oligonucleotide.

The methods of the present invention generally require a knowledge of the target nucleic acid sequence in the region of interest. For example, the region of interest may be that region suspected to contain a point mutation. A minimization of contamination from nucleic acid sequences other than the known target sequence is desired for amplification in the present invention.

The terminal-phosphate-labeled nucleotide useful in the methods and kits of the present invention may be represented by Formula I:

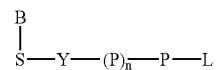

wherein P=phosphate ($PO_3$) and derivatives thereof, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed.

For purposes of the methods of the present invention, useful carbocyclic moieties have been described by Ferraro, M. and Gotor, V. in Chem Rev. 2000, volume 100, 4319–48. Suitable sugar moieties are described by Joeng, L. S. et al., in J Med. Chem. 1993, vol. 356, 2627–38; by Kim H. O. et al., in J Med. Chem. 193, vol. 36, 30–7; and by Eschenmosser A., in Science 1999, vol. 284, 2118–2124. Moreover, useful acyclic moieties have been described by Martinez, C. I., et al., in Nucleic Acids Research 1999, vol. 27, 1271–1274; by Martinez, C. I., et al., in Bioorganic & Medicinal Chemistry Letters 1997, vol. 7, 3013–3016; and in U.S. Pat. No. 5,558,91 to Trainer, G. L. Structures for these moieties are shown below, where for all moieties R may be H, OH, NHR, lower alkyl and aryl; for the sugar moieties X and Y are independently O, S, or NH; and for the acyclic moieties, X=O, S, NH, NR.

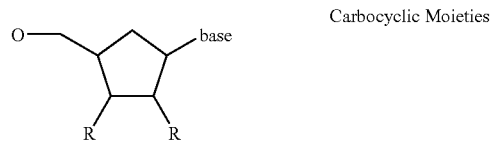

Carbocyclic Moieties

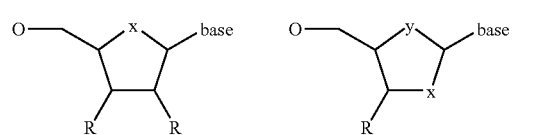

Sugar Moieties

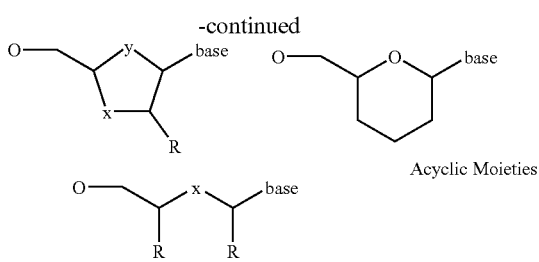

Acyclic Moieties

In certain embodiments, the sugar moiety may be selected from the following: ribosyl, 2'-deoxyribosyl, 3'-deoxyribosyl, 2',3'-dideoxyribosyl, 2', 3'-didehydrodideoxyribosyl, 2'-alkoxyribosyl, 2'-azidoribosyl, 2'-aminoribosyl, 2'-fluororibosyl, 2'mercaptoriboxyl, 2'-alkylthioribosyl, carbocyclic, acyclic and other modified sugars.

Moreover, in Formula I above, the base may include uracil, thymine, cytosine, 5-methylcytosine, guanine, 7-deazaguanine, hypoxanthine, 7-deazahypoxanthine, adenine, 7-deazaadenine, 2,6-diaminopurine or analogs thereof.

The enzyme-activatable label attached at the terminal phosphate position of the nucleotide may be selected from 1,2-dioxetane chemiluminescent compounds, fluorogenic dyes, chromogenic dyes, mass tags, electrochemical tags or combinations thereof. This would allow the detectable species to be detectable by the presence of any one of color, fluorescence emission, chemiluminescence, or a combination thereof.

The enzyme-activatable label may also be a chemical moiety that becomes a substrate for an additional chemical or enzymatic reaction that results in the production of a detectable signal.

Wherein the phosphorylated label shown in Formula I above is a fluorogenic moiety, it is desirably selected from one of the following examples (shown as their phosphate esters): 2-(5'-chloro-2'-phosphoryloxyphenyl)-6-chloro-4-(3H)-quinazolinone, sold under the trade name ELF 97 (Molecular Probes, Inc.), fluorescein diphosphate, fluorescein 3'(6')-O-alkyl-6'(3')-phosphate, 9H-(1,3-dichloro-9,9-dimethylacridin-2-one-7-yl)phosphate, 4-methylumbelliferyl phosphate, resorufin phosphate, 4-trifluoromethylumbelliferyl phosphate, umbelliferyl phosphate, 3-cyanoumbelliferyl phosphate, 9,9-dimethylacirdin-2-one-7-yl phosphate, and 6,8-difluoro-4-methylumbelliferyl phosphate. Structures of these dyes are shown below:

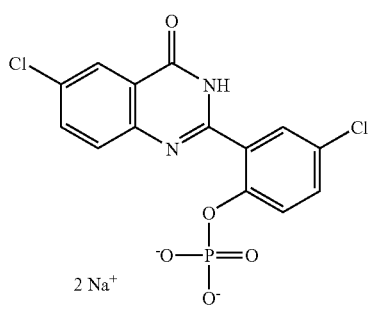

2-(5'-chloro-2'-phosphoryloxyphenyl)-6-chloro-4-(3H)-quinazolinone

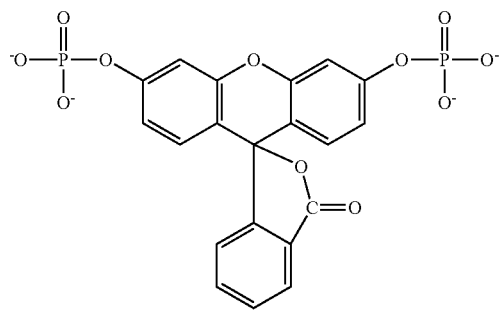

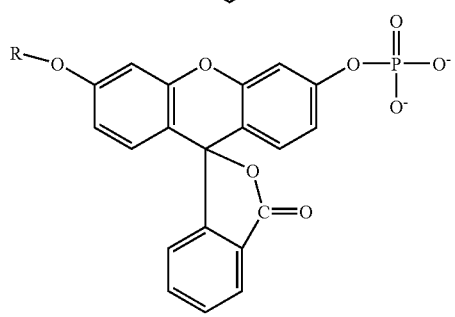

fluorescein diphosphate  fluorescein 3'(6')-O-alkyl-6'(3')-phosphate

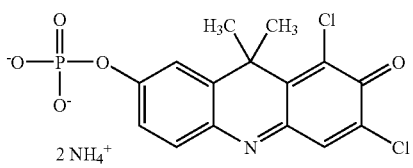

9H-(1,3-dichloro-9,9-dimethylacridin-2-one-7-yl)phosphate (diammonium salt)

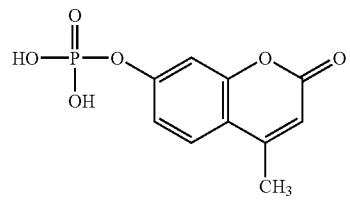

4-methylumbelliferyl phosphate

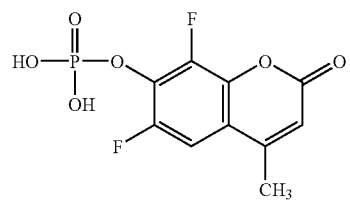

6,8-difluoro-4-methylumbelliferyl phosphate

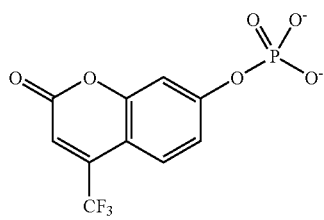

4-Trifluoromethylumbelliferyl phosphate

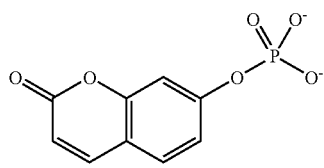

Umbelliferyl phosphate

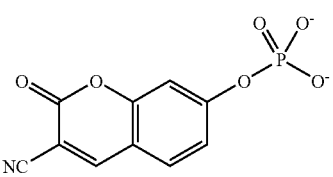

3-Cyanoumbelliferyl phosphate

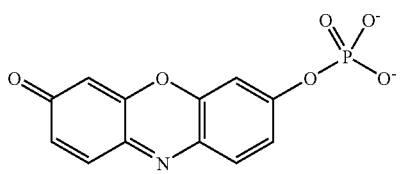

Resorufin phosphate

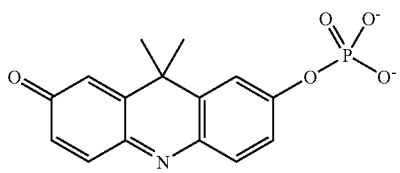

9,9-dimethylacridin-2-one-7-yl phosphate

Wherein the phosphorylated label shown in Formula I above is a chromogenic moiety, it may be selected from the following moieties (shown as the phosphate esters): 5-bromo-4-chloro-3-indolyl phosphate, 3-indolyl phosphate, p-nitrophenyl phosphate and derivatives thereof. The structures of these chromogenic dyes are shown below:

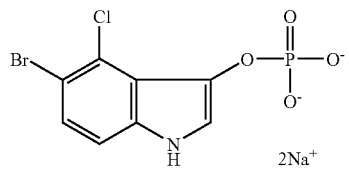

5-bromo-4-chloro-3-indolyl phosphate (disodium salt)

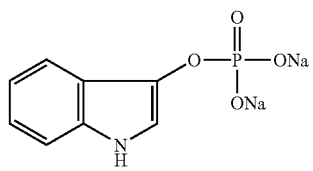

3-indolyl phosphate (disodium salt)

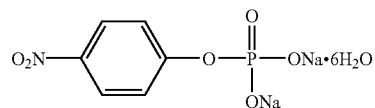

p-nitrophenyl phosphate

The moiety at the terminal phosphate position may further be a chemiluminescent compound wherein it is desired that it is an alkaline phosphatase-activated 1,2-dioxetane compound. The phosphate esters of the 1,2-dioxetane compound may include, but are not limited to, disodium 2-chloro-5-(4-methoxyspiro[1,2-dioxetane-3,2'-(5-chloro-)tricyclo[3,3,1-1$^{3,7}$]-decan]-1-yl)-1-phenyl phosphate, sold under the trade name CDP-Star (Tropix, Inc., Bedford, Mass.), chloroadamant-2'-ylidenemethoxyphenoxy phosphorylated dioxetane, sold under the trade name CSPD (Tropix), and 3-(2'-spiroadamantane)-4-methoxy-4-(3"-phosphoryloxy)phenyl-1,2-dioxetane, sold under the trade name AMPPD (Tropix). The structures of these commercially available dioxetane compounds are disclosed in U.S. Pat. Nos. 5,582,980, 5,112,960 and 4,978,614, respectively, and are shown below:

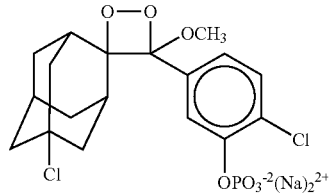

disodium 2-chloro-5-(4-methoxyspiro[1,2-dioxetane-3,2'-(5-chloro-)tricyclo[3,3,1-1$^{3,7}$]-decan]-1-yl)-1-phenyl phosphate

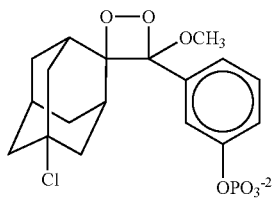

chloroadamant-2'-ylidenemethoxyphenoxy phosphorylated dioxetane,

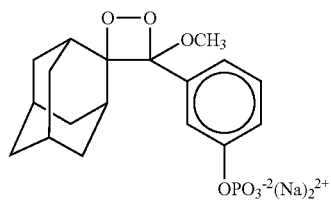

3-(2'-spiroadamantane)-4-methoxy-4-(3"-phosphoryloxy) phenyl-1,2-dioxetane

In the methods of the present invention, the non-hydrolyzable primer should be nuclease-resistant in order to prevent its decomposition by the 3'→5' exonuclease present in the system. As described above, the 3'→5' exonuclease activity may be associated with the DNA polymerase itself. Suitable DNA polymerases for use in the present invention include, but are not limited to, the Klenow fragment of DNA polymerase I, Phi 29 DNA polymerase, DNA polymerase I, T4 DNA polymerase Thermo Sequenase (Amersham Biosciences Corporation), Amplitaq FS (Applied Biosystems), reverse transcriptase, and T7 DNA polymerase.

Methods for synthesizing nuclease-resistant oligonucleotide primers are not particularly limited, and any suitable method known in the art may be used. For example, in one embodiment of the method provided by the invention, the non-hydrolyzable primer is phosphorothioated at the 3'-most phosphodiester linkage terminal. Methods of chemically synthesizing an oligonucleotide primer having nuclease resistance by introducing a phosphorothioate bond into the target site of the primer are well known. In one method, the primer may be chemically synthesized using a modified phosphoramidite method in which the usual oxidation step by iodine water is replaced with an oxidation treatment with a reagent suitable for phosphorothioation, such that a phosphorothioate bond may be introduced in place of the usual phosphodiester bond. One suitable reagent for phosphorothioation is Beaucage's Reagent (3H-1,2-benzodithiole-3-one 1,1-dioxide). This method can be used to introduce a phosphorothioate bond into the primer at any chosen site, including at the 3'-most phosphodiester linkage.

An alternative means of preparing an oligonucleotide primer with a phosphorothioate bond prior to the time of analysis, is via DNA polymerase incorporation of a nucleotide analog in which an oxygen atom at the α-position is replaced by sulfur. Such substituted compounds are referred to as α-S-deoxynucleoside triphosphates. A DNA polymerase can incorporate the sulfur-substituted analog in place of deoxynucleoside triphosphate to give a phosphorothioated oligonucleotide primer containing nuclease resistance.

In any event, the presence of a phosphorothioate bond in place of a phosphodiester bond in the vicinity of the 3'-terminal of the oligonucleotide primer confers a resistance on the part of the primer to an exonuclease cleaving from the 3'-terminal side. The oligonucleotide primer is sufficiently non-hydrolyzable by the introduction of only a single phosphorothioate bond.

Reaction conditions such as buffer, pH, and temperature should be selected to achieve sufficient hybridization, polymerase, nuclease, and phosphatase activities. Temperatures suitable for hybridization depend on the homology between the oligonucleotide primer and the target sequence, but are expected to be in the range of about 20° to about 60° C. The pH values are desired to be in the range of about 7 to 9 in a suitable buffer such as Tris-HCl buffer.

As indicated in the examples below, a target nucleic acid sample must first be denatured by heating at >90° C. for about 5 minutes in a buffered solution containing primer and containing magnesium, followed by hybridization at a suitable temperature for a sufficient period of time, usually about 10 minutes. The hybridization step may be immediately followed by enzymatic treatment at 20–70° C. with DNA polymerase, a 3'→5' exonuclease, which may be associated with a suitable DNA polymerase, and phosphatase in the presence of corresponding substrates.

The present invention is characterized in that following the hybridization step, at least one terminal-phosphate-labeled deoxynucleoside polyphosphate, DNA polymerase, nuclease (which may be associated with the polymerase), and phosphatase are added to the system so that a nucleotide located next to the 3'-terminal of the primer and complimentary to the target nucleic acid is incorporated, followed by decomposition thereof and detection of a detectable species which acts as the signal from the target nucleic acid, the synthesis and decomposition of the complimentary strand being repeated one or more times to effect a cycling assay for amplification of the signal.

It may be helpful to illustrate embodiments of this invention where a single terminal-phosphate-labeled nucleotide is present and, separately, where all four types of terminal-phosphate-labeled nucleotides are present.

The probe becomes hybridized to the target nucleic acid with its 3' end opposite the base immediately adjacent to the specific base being tested for. We can consider by way of example a target sequence in which a base with an asterisk above it represents the point mutation.

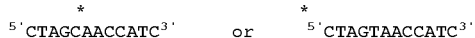

The primer has the following sequence:

A hybrid can be formed as follows:

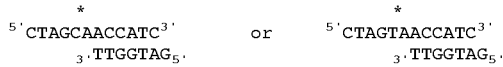

In one format, a terminal-phosphate-labeled dideoxyguanosine polyphosphate is used in the DNA polymerase reaction step of the methods of this invention without any other nucleotide and will be incorporated in one case, but not the other as shown below, where the incorporated nucleotide is underlined:

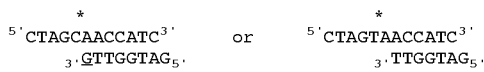

Therefore, the C point mutation may be identified during analysis by the presence of a detectable species formed following phosphatase digestion of the labeled polyphosphate by-product that is concomitantly formed during incorporation of the alkaline-phosphatase-resistant guanosine nucleotide analog. In order to identify the T point mutation in the target sequence, a terminal-phosphate-labeled adenine may be added during a separate analysis for production of a detectable species. As described above, the synthesis and decomposition of the complimentary strand being repeated several times effects the amplification of the signal.

An alternative format provides a means by which any point mutation may be identified during a single analysis. In this format, all four types of terminal-phosphate-labeled nucleotides are present (e.g. adenosine polyphosphate, guanosine polyphosphate, thymidine polyphosphate and cytidine polyphosphate), each bound to a unique dye or label, and each being a non-extendable nucleotide such as terminal-phosphate-labeled dideoxynucleoside triphosphates. In one aspect, the terminal-phosphate-labeled nucleotide is incorporated opposite the specific base of the target. However, as an alternative to using a non-extendable nucleotide, non-terminating nucleotides could also be used provided the length of extension is limited by the presence of more exonuclease than polymerase with the nucleotides used. It is a further aspect that terminal-phosphate-labeled nucleotides used throughout the methods of the present invention are phosphatase-resistant; i.e., only the labeled polyphosphate released as a product serves as the substrate for phosphatase to yield the detectable species. In the assay format using all four types of terminal-phosphate-labeled nucleotides, the identity of the nucleotide adjacent to the 3'-rteminus of the non-hydrolyzable primer can be deduced from the unique color, fluorescence emission, chemiluminescence or other signal obtained from the detectable species.

It is well within the contemplation of the present invention that the amplification reaction could be performed using a polymerase and a single stranded nuclease (which could be an intrinsic property of the polymerase or a separate enzyme). The reaction is thermally cycled, allowing the extension of the primer by polymerase during low temperature, and removal of the added base by nuclease during high temperature. This would allow the user to control the amount of amplification, as it would be dependant on the number of thermal cycles which were performed

EXAMPLES

Example 1

Preparation of δ-9H(1,3-dichloro-9,9-dimethylacridin-2-one-7-yl)-dideoxythymidine-5'-tetraphosphate (ddT4P-DDAO)

ddTTP (100 μl of 80 mM solution) was coevaporated with anhydrous dimethylformamide (DMF, 2×1 ml). To this dicyclohexylcarbodiimide (8.3 mg. 5 eq.) was added and the mixture was again coevaporated with anhydrous DMF (1 ml). Residue was taken in anhydrous DMF (1 ml) and reaction was stirred at room temperature overnight. HPLC showed mostly cyclized triphosphate (~82%). Reaction mixture was concentrated and residue was washed with anhydrous diethyl ether 3×. It was redissolved in anhydrous DMF and concentrated to dryness on rotavap. Residue was taken with DDAO-monophosphate, ammonium salt (5 mg, 1.5 eq.) in 200 μl anhydrous DMF and stirred at 40° C. over the weekend. HPLC showed formation of a new product with desired UV characteristics at 11.96 min. (HPLC Method: 0.30% acetonitrile in 0.1M triethylammonium acetate (pH 7) in 15 min, and 30–50% acetonitrile in 5 min, Novapak C-18 3.9×150 mm column, 1 ml/min). LCMS (ES-) also showed a major mass peak 834 for M-1 peak. Reaction mixture was concentrated and purified on Deltapak C18, 19×300 mm column using 0.1M TEAB (pH 6.7) and acetonitrile. Fraction with product was repurified by HPLC using the same method as described above. Fraction with pure product was concentrated, coevaporated with MeOH (2×) and water (1×). Residue was dissolved in water (1.2 ml) to give a 1.23 mM solution. HPCL purity as 254 nm>97.5%, at 455 nm>96%; UV $\lambda_A$=267 nm and 455 nm; MS: M-1=834.04 (calc 8.33.95).

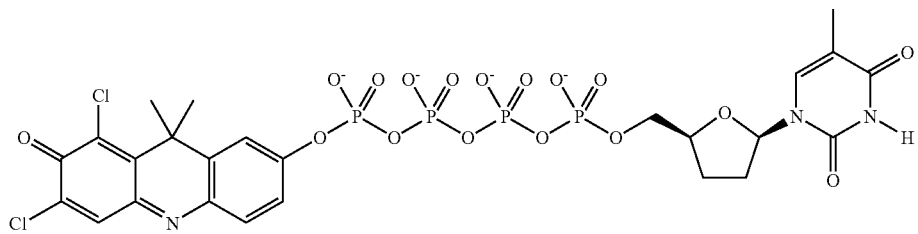

ddT4P-DDAO

Example 2

Preparation of γ (7-Hydroxy-3H-Phenoxazin-3-one)ddGTP (γ-Resorufin-ddGTP)

ddGTP (125 μl of 86.7 mM solution, 10.8 μmol) was coevaporated with anhydrous DMF (3×0.25 ml). To this, DCC (5 eq.) was added and the mixture was again coevaporated with anhydrous DMF (0.25 ml). Residue was taken in anhydrous DMF (1 ml) and the reaction was stirred at room temperature over a weekend. Resorufin (20 eq.) was coevaporated with anhydrous DMF (2×1 ml) and ddGTP trimetaphosphate from the above cyclization step was added, followed by 20 eq. of triethylamine. After 2 weeks, the reaction mixture was concentrated on a rotavap and the residue was extracted with water (3×2 ml) and filtered. The filtrate was purified on an Xterra RP C18 (19×100 mm) column using 0–30% acetonitrile in 0.1 M triethylammonium bicarbonate (pH 6.7) in 5 column volumes and 30–50% acetonitrile in 1 column volume. The pure fraction was concentrated on a rotavap and coevaporated with methanol (2×5 ml). The residue was dissolved in water (1.5 ml) to give a 0.5 mM solution. HPLC purity at 260 nm>98%, at 470 nm>97.5%. UV/VIS=251 and 472 nm. MS: M-1=685.10 (calc. 685.03).

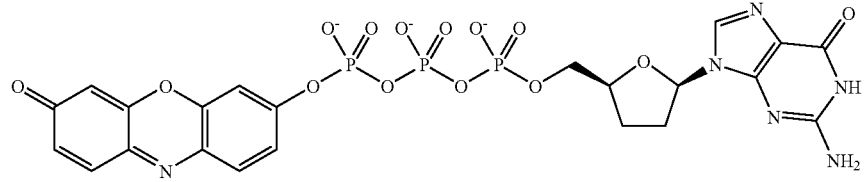

Example 3

Use of Exonuclease III to Amplify Signal Generated by Incorporation of Nucleotides Labeled on the Terminal Phosphate with Fluorogenic Dyes.

Figure 2:
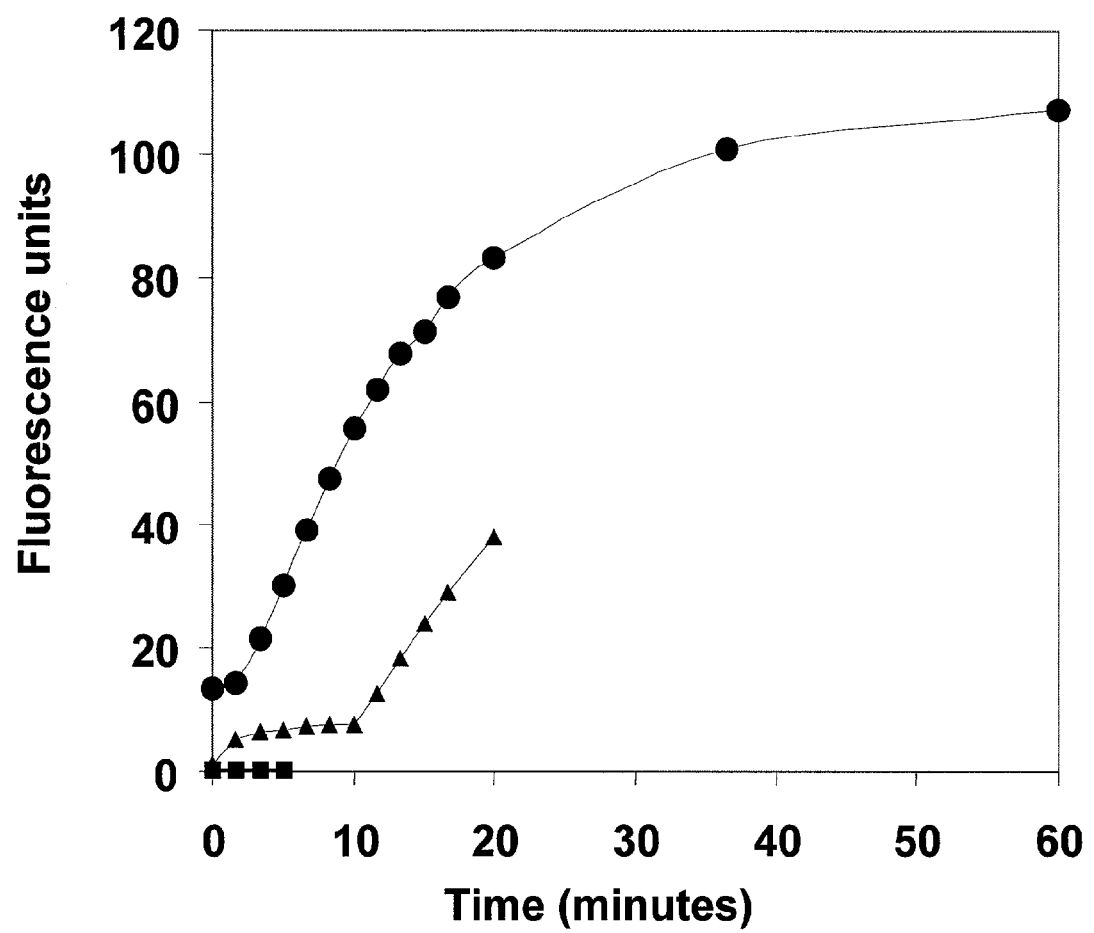
FIG. 2 is a graph of time versus fluorescence emission obtained by the use of a 5'→3' exonuclease to amplify signal generated by incorporation of nucleotides labeled on the terminal phosphate with fluorogenic dyes.

A 50 µl reaction containing 25 mM Tris HCl, pH 8.05 mM MgCl$_2$, 0.5 mM MnSO$_4$, 40 pmoles ddT4P-DDAO (DDAO-δ-2',3'-dideoxythymidine-5'-tetraphosphate), 5 pmoles primer (5'GTTTTCCCAGTCACGACGTTGT*A3' (SEQ ID NO: 1) where * is phosphorothioate linkage) and 10 pmoles template (5'GTCGTTATACAACGTCGTGACTGGGAAAA*ddC3' (SEQ ID NO: 2) where * is phosphorothioate linkage, ddC indicates a terminal dideoxynucleotide) was annealed by heating to 75° for 4 minutes and cooled to 21° C. Referring now to FIG. 2, to this reaction was added the following: 0.15 units shrimp alkaline phosphatase and 0.5 units exonuclease III (squares) or 0.15 units shrimp alkaline phosphatase, 0.5 units exonuclease III, and 16 units Thermo Sequenase (circles). To a third reaction mixture, 0.15 units shrimp alkaline phosphatase and 16 units Thermo Sequenase were added, then after 10 minutes, 0.5 units exonuclease III was added (triangles). Reactions were incubated at room temperature in a quartz fluorescence ultra-microcuvet in an LS-55 Luminescence Spectrophotometer (Perkin Elmer), operated in time drive mode with excitation at 612 nm and emission at 670 nm. Emission is displayed in arbitrary units.

As shown in FIG. 2, no fluorescence emission was obtained from the reaction mixture without polymerase. Moreover, as shown in FIG. 2, amplification of the signal is only obtained when both exonuclease III and polymerase are present in the reaction mixture.

Example 4

Use of Exonuclease III to Amplify Signal Generated by the Sequence Specific Incorporation of Nucleotides Labeled on the Terminal Phosphate with Fluorogenic Dyes with Sequence Specificity.

Figure 3:
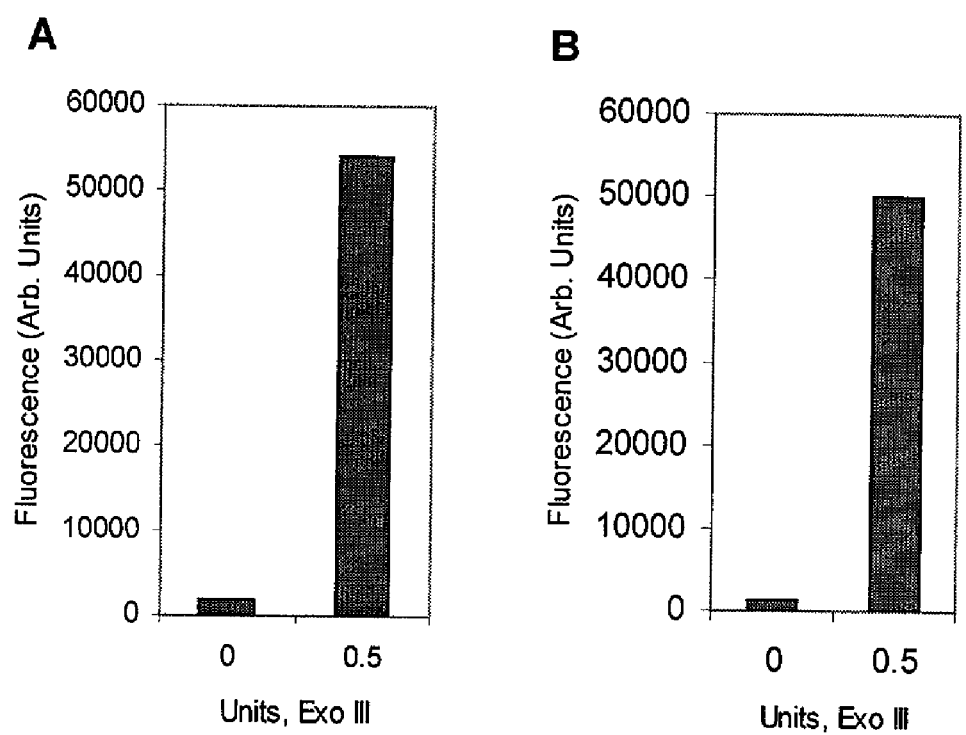
FIG. 3 (A and B) shows bar graphs of the fluorescence emission obtained by the use of a 5'→3' exonuclease to amplify signal generated by the sequence specific incorporation of nucleotides labeled on the terminal phosphate with fluorogenic dyes.

With reference to FIG. 3A, an assay was performed to determine the presence of deoxycytidine (C) in the template. For each result shown in FIG. 3A, a 50 µl reaction containing 25 mM Tris HCl, pH 8.0, 5 mM MgCl$_2$, 0.5 mM MnSO$_4$, 40 pmoles of ddG3P-resorufin (resorufin-γ-2',3'-dideoxyguanosine-5'-triphosphate), 5 pmoles primer (5'GTTTTCCCAGTCACGACGTTGT*A3' (SEQ ID NO: 1) where * is phosphorothioate linkage) and 10 pmoles template (5'GTCGTTCTACAACGTCGTGACTGGGAAAA*ddC3' (SEQ ID NO: 3) where * is phosphorothioate linkage, and ddC indicates a terminal dideoxynucleotide) was annealed by heating to 75° C. for 4 minutes and cooled to 21° C. Thus, for FIG. 3A the primer/template combination was:
5' GTTTTCCCAGTCACGACGTTGTA (SEQ ID NO: 1)
ddCAAAAGGGTCAGTGCTGCAACATCTTGCTG (SEQ ID NO: 3)

To this, 0.15 units shrimp alkaline phosphatase and 16 units Thermo Sequenase DNA polymerase were added, with exonuclease III added as indicated. The reaction was incubated at 21° C. for 40 minutes. After incubation, 25 µl was removed to a 96 well plate and fluorescence was measured in a Tecan ULTRA plate reader with 530 nm excitation and 590 nm emission filters. Fluorescence emission is displayed in arbitrary units.

With reference now to FIG. 3B, an assay was performed to determine the presence of deoxythymidine (T) in the template. For each result shown in FIG. 3B, a 50 µl reaction containing 25 mM Tris HCl, pH 8.0, 5 mM MgCl$_2$, 0.5 mM MnSO$_4$, 40 pmoles of ddT4P-DDAO (DDAO-δ-2',3'-dideoxythymidine-5'-tetraphosphate), 5 pmoles primer (5'GTTTTCCCAGTCACGACGTTGT*A3' (SEQ ID NO: 1) where * is phosphorothioate linkage) and 10 pmoles template (5'GTCGTTATACAACGTCGTGACTGGGAAAA*ddC3' (SEQ ID NO: 2) where * is phosphorothioate linkage, and ddC indicates a terminal dideoxynucleotide) was annealed by heating to 75° C. for 4 minutes and cooled to 21° C. Thus, the primer/template combination was:
5' GTTTTCCCAGTCACGACGTTGTA (SEQ ID NO: 1)
ddCAAAAGGGTCAGTGCTGCAACATATTGCTG (SEQ ID NO: 2)

To this, 0.15 units shrimp alkaline phosphatase and 16 units Thermo Sequenase DNA polymerase were added, with exonuclease III added as indicated. The reaction was incubated at 21° C. for 40 minutes. After incubation, 25 µl was removed to a 96 well plate and fluorescence was measured in a Tecan ULTRA plate reader with 612 nm excitation and 670 nm emission filters. Fluorescence emission is displayed in arbitrary units.

As shown in FIG. 3A, for reactions containing the terminal-phosphate-labeled dideoxyguanosine triphosphate dye, fluorescene emission was detected for the Primer-Template combination where the next nucleotide in the template was a dC. With reference to FIG. 3B, for reactions containing the terminal-phosphate-labeled dideoxythymidine tetraphosphate, fluorescene emission was detected for the Primer-Template combination where the next nucleotide in the template was a dA. Cleavage of the pyrophosphate product of phosphoryl transfer by shrimp alkaline phosphatase leads to a detectable change in the resorufin or DDAO label which allows for the detection of the nucleic acid, the synthesis and degradation of the complementary labeled nucleotide being repeated several times to effect the amplification of the signal.

Having described the particular, desired embodiments of the invention herein, it should be appreciated that modifications may be made therethrough without departing from the contemplated scope of the invention. The true scope of the invention is set forth in the claims appended hereto.

What is claimed is:

1. A method of characterizing a nucleic acid sample comprising the steps of:
    (a) conducting a DNA polymerase reaction, said reaction comprising the reaction of a template, a non-hydrolyzable primer, at least one terminal phosphate-labeled nucleotide, DNA polymerase and an enzyme having 3'→5' exonuclease activity, wherein said enzyme may be selected from the group consisting of DNA polymerases, exonucleases and combinations thereof, which reaction results in the production of labeled polyphosphate;
    (b) permitting said labeled polyphosphate to react with a phosphatase to produce a detectable species characteristic of the sample;
    (c) detecting said detectable species; and
    (d) characterizing said nucleic acid sample based on said detection.

2. The method of claim 1 wherein step (a) further comprises conducting said polymerase reaction in the presence of a phosphatase.

3. The method of claim 1 wherein said detectable species is produced in amounts substantially proportional to the amount of nucleic acid sample.

4. The method of claim 1 further comprising the step of quantifying said nucleic acid sample.

5. The method of claim 1 wherein said nucleic acid sample comprises DNA or RNA.

6. The method of claim 1 wherein step (a) further comprises conducting said polymerase reaction in the presence of two or more terminal phosphate-labeled nucleotides with distinct labels.

7. The method of claim 6 wherein said labels are enzyme-activatable labels selected from the group consisting of chemiluminescent compounds, fluorogenic dyes, chromogenic dyes, mass tags, electrochemical tags and combinations thereof.

8. The method of claim 1 wherein said terminal-phosphate-labeled nucleotide may be represented by formula I:

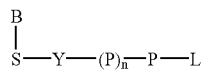

wherein P=phosphate (PO$_3$) and, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed.

9. The method of claim 1, wherein said terminal phosphate-labeled nucleotide comprises four or more phosphate groups in the polyphosphate chain.

10. The method of claim 1 further comprising the step of including one or more additional detection reagents in said polymerase reaction.

11. The method of claim 10 wherein said additional detection reagents are capable of a response that is detectably different from said detectable species.

12. The method of claim 8 wherein said enzyme-activatable label is selected from the group consisting of chemiluminescent compounds, fluorogenic dyes, chromogenic dyes, mass tags, electrochemical tags and combinations thereof.

13. The method of claim 1 wherein said detectable species is detectable by a property selected from the group consisting of color, fluorescence emission, chemiluminescence, mass change, oxidation/reduction potential and combinations thereof.

14. The method of claim 12 wherein said phosphorylated label is a fluorogenic moiety selected from the group consisting of 2-(5'-chloro-2'-phosphoryloxyphenyl)-6-chloro-4-(3H)-quinazolinone, fluorescein diphosphate, fluorescein 3'(6')-O-alkyl-6'(3')-phosphate, 9H-(1,3-dichloro-9,9-dimethylacridin-2-one-7-yl)phosphate, 4-methylumbelliferyl phosphate, resorufin phosphate, 4-trifluoromethylumbelliferylphosphate, umbelliferyl phosphate, 3-cyanoumbelliferyl phosphate, 9,9-dimethylacirdin-2-one-7-yl phosphate and 6,8-difluoro-4-methylumbelliferyl phosphate.

15. The method of claim 12 wherein said phosphorylated label is a chromogenic moiety selected from the group consisting of 5-bromo-4-chloro-3-indolyl phosphate, 3-indoxyl phosphate, p-nitrophenyl phosphate.

16. The method of claim 12 wherein said chemiluminescent compound is an alkaline phosphatase-activated 1,2-dioxetane compound.

17. The method of claim 16 wherein said 1,2-dioxetane compound is selected from the group consisting of 2-chloro-5-(4-methoxyspiro[1,2-dioxetane-3,2-(5-chloro-)tricycle[3,3,1-1$^{3,7}$]-decan]-1-yl)-1-phenyl phosphate, chloroadamant-2'-ylidenemethoxyphenoxyphosphorylated dioxetane, 3-(2'-spiroadamrtre)-4-methoxy-4-(3"-phosphovloxy)phenyl-1,2-dioxetane.

18. The method of claim 8 wherein said sugar moiety is selected from the group consisting of ribosyl, 2'-deoxyribosyl, 3'-deoxyribosyl, 2',3'-dideoxyribosyl, 2',3'-didehydrodideoxyribosyl, 2'-alkoxyribosyl, 2'-azidoribosyl, 2'-aminoribosyl, 2'-fluororibosyl, 2'-mercaptoriboxyl, 2'-alkylthioribosyl, carbocyclic, acyclic and other modified sugars.

19. The method of claim 8 wherein said base is selected from the group consisting of uracil, thymine, cytosine, guanine, 7-deazaguanine, hypoxanthine, 7-deazahypoxanthine, adenine, 7-deazaadenine, 2,6-diaminopurine.

20. The method of claim 1 wherein said non-hydrolyzable primer is a methyl phosphonate, a borano phosphate or is phosphorothioated at the 3'-most phosphodiester linkage.

21. The method of claim 1 wherein said DNA polymerase is selected from the group consisting of the Klenow fragment of DNA polymerase I, Phi 29 DNA polymerase, DNA polymerase I, T4 DNA polymerase, Thermo Sequenase, Amplitaq FS, reverse transcriptase and T7 DNA polymerase.

22. A method of detecting a nucleic acid sample comprising the steps of:
  (a) conducting a DNA polymerase reaction, said reaction comprising the reaction of a template, a non-hydrolyzable primer, at least one terminal phosphate-labeled nucleotide, DNA polymerase and an enzyme having 3'→5' exonuclease activity, wherein said enzyme may be selected from the group consisting of DNA polymerases, exonucleases and combinations thereof, which reaction results in the production of labeled polyphosphate;
  (b) permitting said labeled polyphosphate to react with a phosphatase to produce a detectable species; and
  (c) detecting said detectable species.

23. The method of claim 22 wherein step (a) further comprises conducting said polymerase reaction in the presence of a phosphatase.

24. The method of claim 22 wherein said detectable species is produced in amounts substantially proportional to the amount of nucleic acid sample.

25. The method of claim 22 further comprising the step of quantifying said nucleic acid sample.

26. The method of claim 22 wherein said nucleic acid sample comprises DNA or RNA.

27. The method of claim 22 wherein step (a) further comprises conducting said polymerase reaction in the presence of two or more terminal phosphated-labeled nucleotides with distinct labels.

28. The method of claim 27 wherein said labels are enzyme-activatable labels selected from the group consisting of chemiluminescent compounds, fluorogenic dyes, chromogenic dyes, mass tags, electrochemical tags and combinations thereof.

29. The method of claim 22 wherein said terminal-phosphate-labeled nucleotide may be represented by formula I:

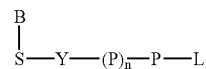

wherein P=phosphate (PO$_3$) and, n is 2 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed.

30. The method of claim 22, wherein said terminal phosphate-labeled nucleotide comprises four or more phosphate groups in the polyphosphate chain.

31. The method of claim 22 further comprising the step of including one or more additional detection reagents in said polymerase reaction.

32. The method of claim 31 wherein said additional detection reagents are capable of a response that is detectably different from said detectable species.

33. The method of claim 29 wherein said enzyme-activatable label is selected from the group consisting of chemiluminescent compounds, fluorogenic dyes, chromogenic dyes, mass tags, electrochemical tags, and combinations thereof.

34. The method of claim 22 wherein said detectable species is detectable by a property selected from the group consisting of color, fluorescence emission, chemiluminescence, mass change, oxidation/reduction potential and combinations thereof.

35. The method of claim 33 wherein said phosphorylated label is a fluorogenic moiety selected from the group consisting of 2-(5'-chloro-2'-phosphoryloxyphenyl)-6-chloro-4-(3H)-quinazolinone, fluorescein diphosphate, fluorescein 3'(6')-O-alkyl-6'(3')-phosphate, 9H-(1,3-dichloro-9,9-dimethylacridin-2-one-7-yl)phosphate, 4-methylumbelliferyl phosphate, resorufin phosphate, 4-trifluoromethylumbelliferylphosphate, umbelliferyl phosphate, 3-cyanoumbelliferyl phosphate, 9,9-dimethylacirdin-2-one-7-yl phosphate, 6,8-difluoro-4-methylumbelliferyl phosphate.

36. The method of claim 33 wherein said phosphorylated label is a chromogenic moiety selected from the group consisting of 5-bromo-4-chloro-3-indolyl phosphate, 3-indoxyl phosphate, p-nitrophenyl phosphate.

37. The method of claim 33 wherein said chemiluminescent compound is a phosphatase-activated 1,2-dioxetane compound.

38. The method of claim 37 wherein said 1,2-dioxetane compound is selected from the group consisting of 2-chloro-5-(4-meloxyspiro[1,2-dioxetane-3,2-(5-chloro-)tricycle[3,3,1-1$^{3,7}$]-decan]-1-yl)-1-phenyl phosphate, chloroadamant-2'-ylidenemethoxyphenoxyphosphorylated dioxetane and 3-(2'-spiroadamrtre)-4-methoxy-4-(3"-phosphovloxy)phenyl-1,2-dioxetane.

39. The method of claim 29 wherein said sugar moiety is selected from the group consisting of ribosyl, 2'-deoxyribosyl, 3'-deoxyribosyl, 2',3'-dideoxyribosyl, 2',3'-didehydrodideoxy-ribosyl, 2'-alkoxyribosyl, 2'-azidoribosyl, 2'-aminoribosyl, 2'-fluororibosyl, 2'mercaptoriboxyl, 2'-alkylthioribosyl, carbocyclic, acyclic and other modified sugars.

40. The method of claim 29 wherein said base is selected from the group consisting of uracil, thymine, cytosine, guanine, 7-deazaguanine, hypoxanthine, 7-deazahypoxanthine, adenine, 7-deazaadenine, 2,6-diaminopurine.

41. The method of claim 22 wherein said non-hydrolyzable primer is a methyl phosphonate, a borano phosphate or is phosphorothioated at the 3'-most phosphodiester linkage.

42. The method of claim 22 wherein said DNA polymerase is selected from the group consisting of the Klenow fragment of DNA polymerase I, Phi 29 DNA polymerase, DNA polymerase I, T4 DNA polymerase, Thermo Sequenase, Amplitaq FS, reverse transcriptase and T7 DNA polymerase.

43. A method of characterizing a nucleic acid sample comprising the steps of:
  (a) conducting a DNA polymerase reaction, said reaction comprising the reaction of a template, a non-hydrolyzable primer, at least one terminal phosphate-labeled nucleotide having four or more phosphate groups in the polyphosphate chain, DNA polymerase and an enzyme having 3'→5' exonuclease activity, wherein said enzyme may be selected from the group consisting of DNA polymerases, exonucleases and combinations thereof, which reaction results in the production of labeled polyphosphate;
  (b) detecting said labeled polyphosphate; and
  (c) characterizing the nucleic acid sample based on said detection.

44. A method of characterizing a nucleic acid sample comprising the steps of:
  (a) conducting a DNA polymerase reaction, said reaction comprising the reaction of a template, a non-hydrolyzable primer, at least one terminal phosphate-labeled nucleotide having four or more phosphate groups in the polyphosphate chain, DNA polymerase and an enzyme having 3'→5' exonuclease activity, wherein said enzyme may be selected from the group consisting of DNA polymerases, exonucleases and combinations thereof, which reaction results in the production of labeled polyphosphate;
  (b) permitting said labeled polyphosphate to react with a phosphatase to produce a detectable species having a signal profile characteristic of the sample;
  (c) detecting said detectable species; and
  (d) characterizing said nucleic acid sample based on said signal profile.

45. A method of detecting a nucleic acid sample comprising the steps of:
  (a) conducting a DNA polymerase reaction, said reaction comprising the reaction of a template, a non-hydrolyzable primer, at least one terminal phosphate-labeled nucleotide having four or more phosphate groups in the polyphosphate chain, DNA polymerase and an enzyme having 3'→5' exonuclease activity, wherein said enzyme may be selected from the group consisting of DNA polymerases, exonucleases and combinations thereof, which reaction results in the production of labeled polyphosphate; and
  (b) detecting said labeled polyphosphate.

46. A method of detecting a nucleic acid sample comprising the steps of:
  (a) conducting a DNA polymerase reaction, said reaction comprising the reaction of a template, a non-hydrolyzable primer, at least one terminal phosphate-labeled nucleotide having four or more phosphate groups in the polyphosphate chain, DNA polymerase and an enzyme having 3'→5' exonuclease activity, wherein said enzyme may be selected from the group consisting of DNA polymerases, exonucleases and combinations thereof, which reaction results in the production of labeled polyphosphate;
  (b) permitting said labeled polyphosphate to react with a phosphatase to produce a detectable species; and
  (c) detecting said detectable species.

* * * * *